US009417182B2

(12) United States Patent
Akiyama et al.

(10) Patent No.: US 9,417,182 B2
(45) Date of Patent: Aug. 16, 2016

(54) PRISM MEMBER, TERAHERTZ-WAVE SPECTROSCOPIC MEASUREMENT DEVICE, AND TERAHERTZ-WAVE SPECTROSCOPIC MEASUREMENT METHOD

(71) Applicant: HAMAMATSU PHOTONICS K.K., Hamamatsu-shi, Shizuoka (JP)

(72) Inventors: Kouichiro Akiyama, Hamamatsu (JP); Takashi Yasuda, Hamamatsu (JP); Yoichi Kawada, Hamamatsu (JP); Atsushi Nakanishi, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 14/402,570

(22) PCT Filed: May 2, 2013

(86) PCT No.: PCT/JP2013/062765
§ 371 (c)(1),
(2) Date: Nov. 20, 2014

(87) PCT Pub. No.: WO2013/179856
PCT Pub. Date: Dec. 5, 2013

(65) Prior Publication Data
US 2015/0136986 A1   May 21, 2015

(30) Foreign Application Priority Data

May 29, 2012   (JP) .................. 2012-121923

(51) Int. Cl.
*G01N 21/35*   (2014.01)
*G01N 21/3586*   (2014.01)
*G01N 21/3581*   (2014.01)

(52) U.S. Cl.
CPC ........ *G01N 21/3586* (2013.01); *G01N 21/3581* (2013.01)

(58) Field of Classification Search
CPC .................. G01N 21/3586; G01N 21/3581
See application file for complete search history.

(56) References Cited

U.S. PATENT DOCUMENTS

| 4,964,705 A | * | 10/1990 | Markle | .................. 359/727 |
| 2006/0231762 A1 | * | 10/2006 | Ohtake | ............... G01N 21/552 |
| | | | | 250/341.8 |
| 2007/0196055 A1 | * | 8/2007 | Kato et al. | ..................... 385/78 |

FOREIGN PATENT DOCUMENTS

| EP | 2 693 200 | 2/2014 |
| GB | 664754 | 1/1952 |

(Continued)

OTHER PUBLICATIONS

Machine Translation of JP 2008-224451.*

(Continued)

*Primary Examiner* — Yara B Green
(74) *Attorney, Agent, or Firm* — Drinker Biddle & Reath LLP

(57) ABSTRACT

A prism member having an entrance surface for arranging a terahertz-wave generator for generating a terahertz wave in response to pump light incident thereon, an arrangement part for arranging an object to be measured, an exit surface for arranging a terahertz-wave detector for detecting a correlation between the terahertz wave transmitted through the object in the arrangement part and probe light, a first optical surface for collimating or condensing the terahertz wave incident thereon from the entrance surface toward the arrangement part, and a second optical surface for condensing the terahertz wave transmitted through the arrangement part toward the exit surface, the arrangement part forms a depression adapted to be filled with a liquid incapable of dissolving the object therein.

12 Claims, 10 Drawing Sheets

(56) References Cited

FOREIGN PATENT DOCUMENTS

| JP | 200-304690 | | 11/2000 |
|---|---|---|---|
| JP | 2003-529760 A | | 10/2003 |
| JP | 2004-093495 | * | 3/2004 |
| JP | 2006-184078 A | | 7/2006 |
| JP | 2007-279025 | * | 3/2007 |
| JP | 2008-224449 A | | 9/2008 |
| JP | 2008-224451 A | | 9/2008 |
| JP | 2008-224452 | | 9/2008 |
| JP | 2010-164511 A | | 7/2010 |
| JP | 2012-083166 | | 4/2012 |
| JP | 2012-088197 | | 5/2012 |
| WO | WO 02/18919 | * | 7/2002 |
| WO | WO-2010/073604 A1 | | 7/2010 |
| WO | WO-2012/132647 A1 | | 10/2012 |

OTHER PUBLICATIONS

Machine Translation JP 2004-093495.*
Machine Translation JP 2007-279025.*
David J. Cook, et al., "Through Container THz sensing: applications for explosives screening," Proceedings of SPIE, vol. 5354 [Terahertz and Gigahertz Electronics and Photonics III], Jan. 26, 2004, pp. 55-62.
English-language translation of International Preliminary Report on Patentability (IPRP) dated Dec. 11, 2014 that issued in WO Patent Application No. PCT/JP2013/062765.

* cited by examiner

PRISM MEMBER, TERAHERTZ-WAVE SPECTROSCOPIC MEASUREMENT DEVICE, AND TERAHERTZ-WAVE SPECTROSCOPIC MEASUREMENT METHOD

TECHNICAL FIELD

The present invention relates to a prism member for use in transmission spectrometry employing a terahertz wave and a terahertz-wave spectrometer and terahertz-wave spectrometric method using the same.

BACKGROUND ART

Conventionally known as an example of techniques relating to a spectrometer using a terahertz wave is a terahertz-wave spectrometer described in Patent Literature 1. In this terahertz-wave spectrometer, an entrance surface of an internal total reflection prism is integrally provided with a terahertz-wave generator, while an exit surface of the internal total reflection prism is integrally provided with a terahertz-wave detector. Using such an integral prism integrating the internal total reflection prism, terahertz-wave generator, and terahertz-wave detector together is advantageous in that it can detect terahertz waves at high efficiency while reducing the size of the total reflection spectrometer.

An example of detection devices for performing transmission spectrometry which detects the state of a terahertz wave transmitted through an object to be measured is one disclosed in Patent Literature 2. In this detection device, both end faces of a multilayer body formed by holding both sides of a polystyrene sheet with metal sheets are provided with a terahertz-wave generator and a terahertz-wave detector. A void having a rectangular cross section is formed at a center part of the polystyrene sheet, so as to be filled with an object to be measured.

CITATION LIST

Patent Literature

Patent Literature 1: Japanese Patent Application Laid-Open No. 2008-224449
Patent Literature 2: Japanese Patent Application Laid-Open No. 2006-184078

SUMMARY OF INVENTION

Technical Problem

When measuring the state of a terahertz wave transmitted through an object to be measured, if the terahertz wave passes through air, the measurement accuracy may decrease under the influence of absorption by moisture in the air or the reflection loss at the interface between a waveguide member and the air. On the other hand, there is a case where the terahertz wave is transmitted through the object as collimated or condensed light. Hence, there has been a demand for contrivances for enabling measurement suppressing the above-mentioned influences of absorption and reflection loss regardless of the form of the part where the object is placed or the shape of the object.

It is an object of the present invention to provide a prism member which can improve the measurement accuracy of spectrometry regardless of the shape of the object and a terahertz-wave spectrometer and terahertz-wave spectrometric method using the same.

Solution to Problem

The prism member in accordance with the present invention is a prism member for use in transmission spectrometry of an object to be measured employing a terahertz wave, the prism member comprising an entrance surface for arranging a terahertz-wave generator for generating a terahertz wave in response to pump light incident thereon, an arrangement part for arranging the object, an exit surface for arranging a terahertz-wave detector for detecting a correlation between the terahertz wave transmitted through the object in the arrangement part and probe light, a first optical surface for collimating or condensing the terahertz wave incident thereon from the entrance surface toward the arrangement part, and a second optical surface for condensing the terahertz wave transmitted through the arrangement part toward the exit surface, while the arrangement part forms a depression adapted to be filled with a liquid incapable of dissolving the object therein.

In this prism member, the arrangement part for arranging the object is a depression which can be filled with a liquid incapable of dissolving the object therein. Therefore, in a path of the terahertz wave impinging on the first optical surface and then passing through the arrangement part toward the second optical surface, the terahertz wave can be kept from traveling through air. This can eliminate the influence of absorption by the moisture in the air, thereby improving the measurement accuracy in spectrometry. The depression may have various forms depending on the shape of the object and the like but can easily be filled with a liquid regardless of the forms, whereby the convenience of measurement is maintained.

The depression may include a first refractive surface for refracting the terahertz wave from the first optical surface toward the object and a second refractive surface for refracting the terahertz wave transmitted through the object toward the second optical surface. When refracting light at an interface between media having different refractive indexes, appropriately setting the angle of incidence with respect to the interface can reduce reflection loss as compared with the case where the light is perpendicularly incident on the interface and transmitted therethrough without refraction. Therefore, the reflection loss of the terahertz wave directed from the first optical surface to the object can be reduced when the depression includes the first refractive surface, while the reflection loss of the terahertz wave passing through the object toward the second optical surface can be reduced when the depression includes the second refractive surface. This can more securely eliminate the influence of the reflection loss of the terahertz wave, thereby further improving the measurement accuracy in spectrometry.

The object may be a solid, while the arrangement part may have a support part for supporting the object. This can stabilize the posture of the object within the arrangement part when the object is a solid, thereby further improving the measurement accuracy.

The object may be a liquid, while the arrangement part may have a support part for supporting a cell containing the object. This makes the object easy to arrange into and take out from the arrangement part when the object is a liquid.

The terahertz-wave spectrometer in accordance with the present invention is a terahertz-wave spectrometer for performing transmission spectrometry of an object to be measured by using a terahertz wave, the spectrometer comprising a light source for emitting laser light, a branching unit for splitting the laser light emitted from the light source into pump light and probe light, and a prism member; the prism member having an entrance surface for arranging a terahertz-wave generator for generating a terahertz wave in response to the pump light incident thereon, an arrangement part for arranging the object, an exit surface for arranging a terahertz-wave detector for detecting a correlation between the terahertz wave transmitted through the object in the arrangement part and the probe light, a first optical surface for collimating or condensing the terahertz wave incident thereon from the entrance surface toward the arrangement part, and a second optical surface for condensing the terahertz wave transmitted through the arrangement part toward the exit surface, while the arrangement part forms a depression adapted to be filled with a liquid incapable of dissolving the object therein.

In this terahertz-wave spectrometer, the arrangement part for arranging the object in the prism member is a depression which can be filled with a liquid incapable of dissolving the object therein. Therefore, in a path of the terahertz wave impinging on the first optical surface and then passing through the arrangement part toward the second optical surface, the terahertz wave can be kept from traveling through air. This can eliminate the influence of absorption by the moisture in the air, thereby improving the measurement accuracy in spectrometry. The depression may have various forms depending on the shape of the object and the like but can easily be filled with a liquid regardless of the forms, whereby the convenience of measurement is maintained.

The depression may include a first refractive surface for refracting the terahertz wave from the first optical surface toward the object and a second refractive surface for refracting the terahertz wave transmitted through the object toward the second optical surface. When refracting light at an interface between media having different refractive indexes, appropriately setting the angle of incidence with respect to the interface can reduce reflection loss as compared with the case where the light is perpendicularly incident on the interface and transmitted therethrough without refraction. Therefore, the reflection loss of the terahertz wave directed from the first optical surface to the object can be reduced when the depression includes the first refractive surface, while the reflection loss of the terahertz wave passing through the object toward the second optical surface can be reduced when the depression includes the second refractive surface. This can more securely eliminate the influence of the reflection loss of the terahertz wave, thereby further improving the measurement accuracy in spectrometry.

The object may be a solid, while the arrangement part may have a support part for supporting the object. This can stabilize the posture of the object within the arrangement part when the object is a solid, thereby further improving the measurement accuracy.

The object may be a liquid, while the arrangement part may have a support part for supporting a cell containing the object. This makes the object easy to arrange into and take out from the arrangement part when the object is a liquid.

The terahertz-wave spectrometric method in accordance with the present invention is a terahertz-wave spectrometric method for performing transmission spectrometry of an object to be measured by using a terahertz wave, the method using a prism member having an entrance surface for arranging a terahertz-wave generator for generating a terahertz wave in response to pump light incident thereon, an arrangement part for arranging the object, an exit surface for arranging a terahertz-wave detector for detecting a correlation between the terahertz wave transmitted through the object in the arrangement part and probe light, a first optical surface for collimating or condensing the terahertz wave incident thereon from the entrance surface toward the arrangement part, and a second optical surface for condensing the terahertz wave transmitted through the arrangement part toward the exit surface, the arrangement part forming a depression adapted to be filled with a liquid incapable of dissolving the object therein; the method comprising arranging the object in a state where the depression is filled with the liquid incapable of dissolving the object therein; and measuring an optical constant concerning the object according to the terahertz wave transmitted through the object.

This terahertz-wave spectrometric method performs spectrometry by using a prism member whose arrangement part for arranging the object is a depression and filling the depression with a liquid incapable of dissolving the object. Therefore, in a path of the terahertz wave impinging on the first optical surface and then passing through the arrangement part toward the second optical surface, the terahertz wave can be kept from traveling through air. This can eliminate the influence of absorption by the moisture in the air, thereby improving the measurement accuracy in spectrometry. The depression may have various forms depending on the shape of the object and the like but can easily be filled with a liquid regardless of the forms, whereby the convenience of measurement is maintained.

The prism member having the arrangement part constituted by the depression including a first refractive surface for refracting the terahertz wave from the first optical surface toward the object and a second refractive surface for refracting the terahertz wave transmitted through the object toward the second optical surface may be used. When refracting light at an interface between media having different refractive indexes, appropriately setting the angle of incidence with respect to the interface can reduce reflection loss as compared with the case where the light is perpendicularly incident on the interface and transmitted therethrough without refraction. Therefore, the reflection loss of the terahertz wave directed from the first optical surface to the object can be reduced when the depression includes the first refractive surface, while the reflection loss of the terahertz wave passing through the object toward the second optical surface can be reduced when the depression includes the second refractive surface. This can more securely eliminate the influence of the reflection loss of the terahertz wave, thereby further improving the measurement accuracy in spectrometry.

The object may be a solid, and the prism member having a support part for supporting the object in the arrangement part may be used. This can stabilize the posture of the object within the arrangement part when the object is a solid, thereby further improving the measurement accuracy.

The object may be a liquid, and the prism member having a support part for supporting a cell containing the object may be used. This makes the object easy to arrange into and take out from the arrangement part when the object is a liquid.

As the liquid incapable of dissolving the object therein, a liquid incapable of absorbing the terahertz wave may be used. This inhibits the liquid from absorbing the terahertz wave and thus can measure the optical constant concerning the object more accurately.

As the liquid incapable of dissolving the object therein, a fluorine-based inert liquid may be used. In this case, using the fluorine-based inert liquid makes many substances insoluble to the liquid and inhibits the liquid from absorbing the terahertz wave. The fluorine-based inert liquid is hard to vaporize and thus prevents volatile ingredients from adversely affecting the surroundings, while suppressing environmental load.

As the liquid incapable of dissolving the object therein, a silicone oil may be used. In this case, using the silicone oil makes many substances insoluble to the liquid and inhibits the liquid from absorbing the terahertz wave. The silicone oil

DESCRIPTION OF EMBODIMENTS

In the following, preferred embodiments of the prism member, terahertz-wave spectrometer, and terahertz-wave spectrometric method in accordance with the present invention will be explained in detail with reference to the drawings.

Figure 1:
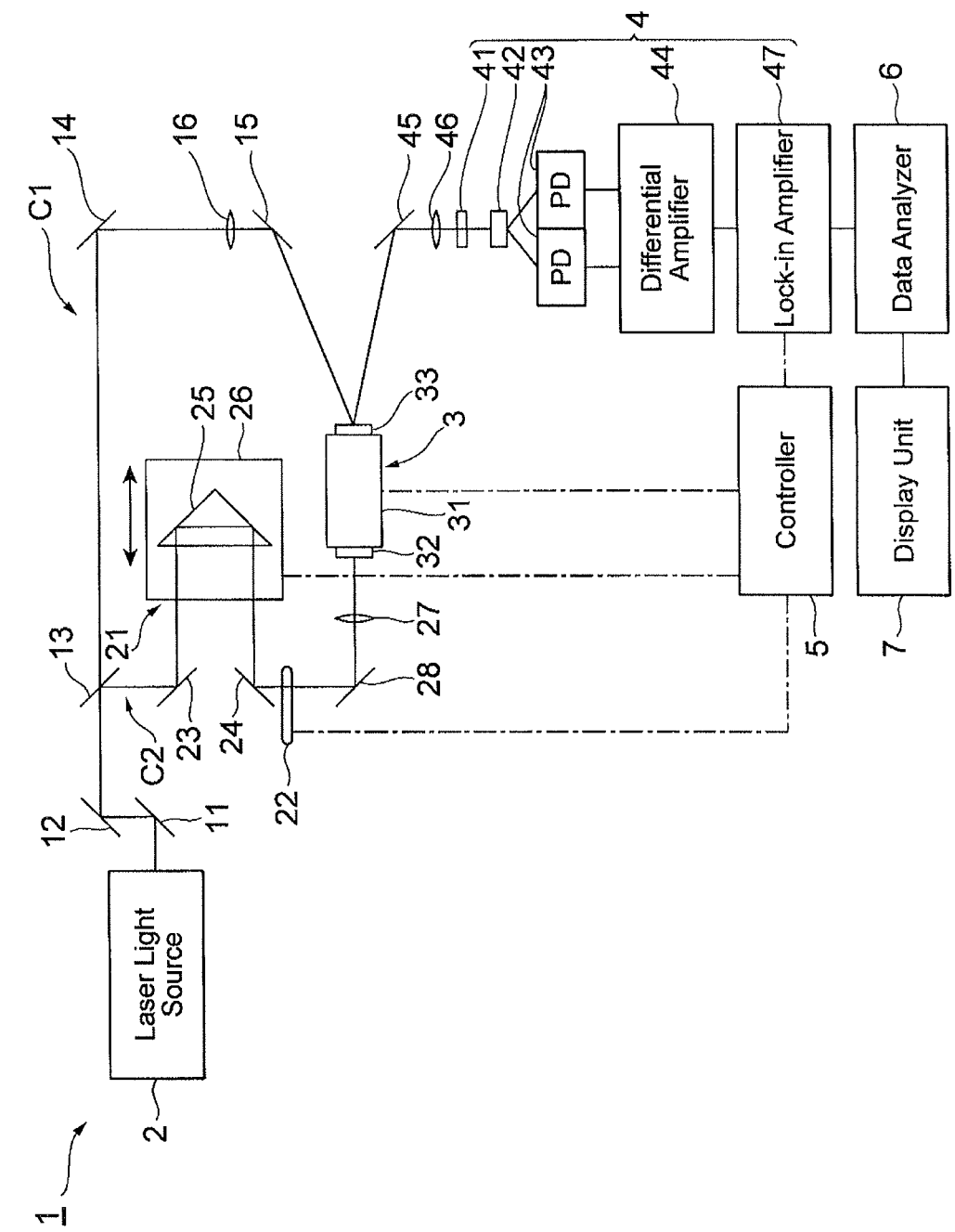
FIG. 1 is a diagram illustrating an embodiment of the terahertz-wave spectrometer in accordance with the present invention.

FIG. 1 is a diagram illustrating an embodiment of the terahertz-wave spectrometer in accordance with the present invention. As depicted, this terahertz-wave spectrometer 1 comprises a laser light source 2 for emitting laser light, an integral prism 3 in which a terahertz-wave generator 32, a spectroscopic prism (prism member) 31, and a terahertz-wave detector 33 are integrated together, and a detection unit 4 for detecting a terahertz wave. The terahertz-wave spectrometer 1 also comprises a controller 5 for controlling operations of the constituents mentioned above, a data analyzer 6 for analyzing data according to an output from the detection unit 4, and a display unit 7 for displaying results of processing in the data analyzer 6.

The laser light source 2 is a light source for generating a femtosecond pulsed laser. The laser light source 2 issues a femtosecond pulsed laser having an average power of 120 mW and a repetition rate of 77 MHz, for example. The femtosecond pulsed laser emitted from the laser light source 2 impinges on mirrors 11, 12 in sequence and then is split into two, i.e., pump light 48 and probe light 49, by a beam splitter 13 (see FIG. 2). A probe light optical path C1 through which the probe light 49 propagates is provided with mirrors 14, 15 and a lens 16, so that the probe light 49 is condensed by the lens 16, so as to be made incident on the terahertz-wave detector 33 which will be explained later.

On the other hand, a pump light optical path C2 through which the pump light 48 propagates is provided with a delay unit 21 and a modulator 22. The delay unit 21, which is constructed by a pair of mirrors 23, 24 and a reflection prism 25 disposed on a movable stage 26, can adjust a delay in the pump light 48 by moving the position of the reflection prism 25 back and forth with respect to the pair of mirrors 23, 24. The modulator 22 is a part which switches between transmitting and blocking the pump light 48 by an optical chopper, for example. According to a signal from the controller 5, the modulator 22 modulates the switching between transmitting and blocking the pump light 48 at 1 kHz, for example.

Figure 2:
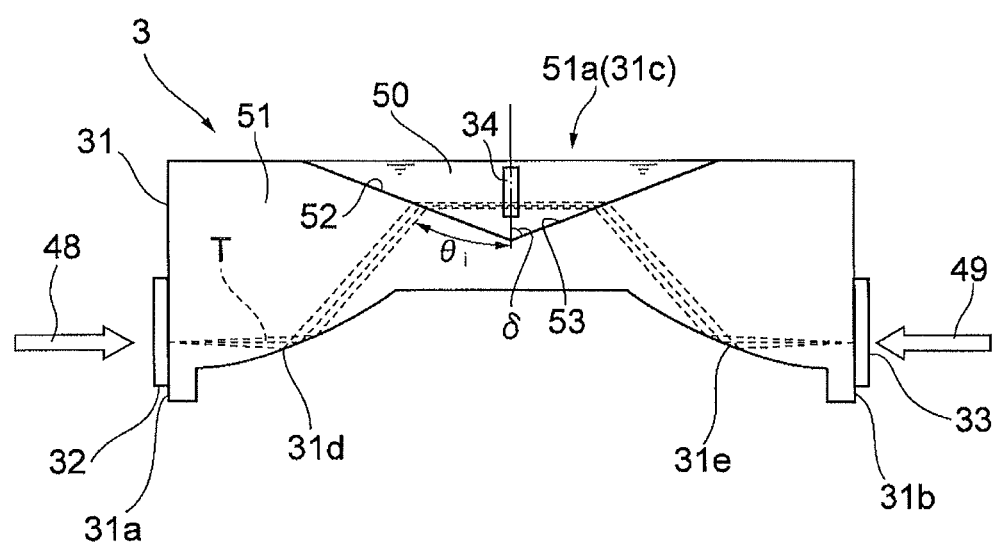
FIG. 2 is a side view of an integral prism used in the terahertz-wave spectrometer illustrated in FIG. 1.

The pump light 48 propagated through the pump light optical path C2 impinges on a mirror 28 and then is condensed by a lens 27, so as to be made incident on the integral prism 3. As illustrated in FIG. 2, the spectroscopic prism 31 constituting the integral prism 3, which is formed by Si, for example, has an entrance surface 31a to which the terahertz-wave generator 32 is integrally secured and an exit surface 31b to which the terahertz-wave detector 33 is integrally secured. The upper face of the spectroscopic prism 31 forms an arrangement part 31c to be arranged with an object to be measured 34, from which various optical constants such as refractive index, dielectric constant, and absorption coefficient are measured.

In the bottom face of the spectroscopic prism 31, as illustrated in FIG. 2, a first optical surface 31d for collimating a terahertz wave T generated in the terahertz-wave generator 32 toward the arrangement part 31c is provided between the entrance surface 31a and the arrangement part 31c. A second optical surface 31e for condensing the terahertz wave T from the arrangement part 31c toward the exit surface 31b is provided between the arrangement part 31c and the exit surface 31b. The first and second optical surfaces 31d, 31e are formed by curving the bottom face of the spectroscopic prism 31 into a predetermined form.

Nonlinear optical crystals of ZnTe and the like, antenna elements such as optical switches using GaAs, semiconductors such as InAs, and superconductors, for example, can be used as the terahertz-wave generator 32. The pulse of the terahertz wave T generated from these elements is in the order of several picoseconds in general. When a nonlinear optical crystal is used as the terahertz-wave generator 32, the pump light 48 incident on the terahertz-wave generator 32, if any, is converted into the terahertz wave T by a nonlinear optical effect.

Electrooptical crystals of ZnTe and the like and antenna elements such as optical switches using GaAs, for example, can be used as the terahertz-wave detector 33. When the terahertz wave T and the probe light 49 are incident on the terahertz-wave detector 33 at the same time in the case where an electrooptical crystal is used as the terahertz-wave detector 33, the probe light 49 incurs birefringence due to the Pockels effect. The amount of birefringence in the probe light 49 is in proportion to the electric field intensity of the terahertz wave T. Therefore, detecting the amount of birefringence of the probe light 49 makes it possible to detect the terahertz wave T.

For example, a thermosetting adhesive is used for securing the terahertz-wave generator 32 and the terahertz-wave detector 33. Preferably, the adhesive used here is transparent at the wavelength of the terahertz wave T and has a refractive index in the middle between or equivalent to each of the respective refractive indexes of the terahertz-wave generator 32 and terahertz-wave detector 33 and the refractive index of the spectroscopic prism 31.

A wax transparent at the wavelength of the terahertz wave T may be melted and coagulated in place of the adhesive, or marginal parts of the terahertz-wave generator 32 and terahertz-wave detector 33 may be secured with the adhesive while the terahertz-wave generator 32 and terahertz-wave detector 33 are in direct contact with the entrance surface 31a and exit surface 31b, respectively.

When the terahertz-wave detector 33 is an electrooptical crystal, the detection unit 4 for detecting the terahertz wave is constituted by a quarter wave plate 41, a polarizer 42, a pair of photodiodes 43, 43, a differential amplifier 44, and a lock-in amplifier 47, for example, as illustrated in FIG. 1. The probe light 49 reflected by the terahertz-wave detector 33 is guided by the mirror 45 toward the detection unit 4, condensed by a lens 46, so as to be transmitted through the quarter wave plate 41, and then separated by the polarizer 42, which is a Wollaston prism or the like, into vertical and horizontal linearly polarized light components. The vertical and horizontal linearly polarized light components of the probe light 49 are converted into their respective electric signals by the pair of photodiodes 43, 43, while the difference therebetween is detected by the differential amplifier 44. The output signal from the differential amplifier 44 is amplified by the lock-in amplifier 47 and then fed to the data analyzer 6.

The differential amplifier 44 outputs a signal having an intensity in proportion to the electric field intensity of the terahertz wave T when the terahertz wave T and the probe light 49 are incident on the terahertz-wave detector 33 at the same time, but no signal when not. The amplitude and phase of the terahertz wave T in the arrangement part 31c of the spectroscopic prism 31 vary depending on the object 34 arranged in the arrangement part 31c. Therefore, measuring the change in amplitude and phase of the terahertz wave T can evaluate the spectroscopic characteristic of the object 34.

The data analyzer 6 is a part which performs data analysis processing of transmission spectrometry according to an analysis program exclusively used by the terahertz-wave spectrometer 1, for example, and is physically a computer system having a CPU (central processing unit), a memory, an input device, the display unit 7, and the like. The data analyzer 6 executes data analysis processing according to a signal fed from the lock-in amplifier 47 and causes the display unit 7 to display results of analysis.

The structure of the arrangement part 31c of the above-mentioned integral prism 3 will now be explained further in detail.

As illustrated in FIG. 2, the arrangement part 31c of the integral prism 3 is constructed by a depression 51a having a triangular cross section formed between side faces of the integral prism 3. The depression 51a has a first refractive surface 52 for refracting the terahertz wave T from the first optical surface 31d toward the object 34 and a second refractive surface 53 for refracting the terahertz wave T transmitted through the object 34 toward the second optical surface 31e.

The depression 51a is filled with a liquid 50. The liquid 50 is required to be incapable of dissolving the object 34 therein and preferably does not absorb the terahertz wave T. As the liquid 50, a fluorine-based inert liquid, a silicone oil, or the like is used. Examples of the fluorine-based inert liquid include perfluorocarbon, hydrofluorocarbon, and perfluoropolyether.

Among these liquids, perfluorocarbon is preferred in particular in its insolubility and absorbability. Fluorine-based inert liquids and silicone oils are preferred in that they are hard to vaporize and thus prevent volatile ingredients from adversely affecting the surroundings, while suppressing environmental load. By "incapable of absorbing the terahertz wave" is meant herein that the absorbing coefficient for terahertz waves at 0.1 THz to 10 THz is 20 cm$^{-1}$ or less, more preferably 10 cm$^{-1}$ or less, for example.

When the spectroscopic prism 31 is made of Si having a refractive index of 3.4, the refractive index of the liquid 50 filling the depression 51a is 1.4, and the incidence angle θi of the terahertz wave T with respect to the spectroscopic prism 31 is 45°, the opening angle δ of the depression 51a having the triangular cross section is 67.3°, for example. Any jig (not depicted) may be used for holding the object 34 within the depression 51a. The object 34 is held substantially orthogonal to the terahertz wave T entering the arrangement part 31c.

Figure 3:
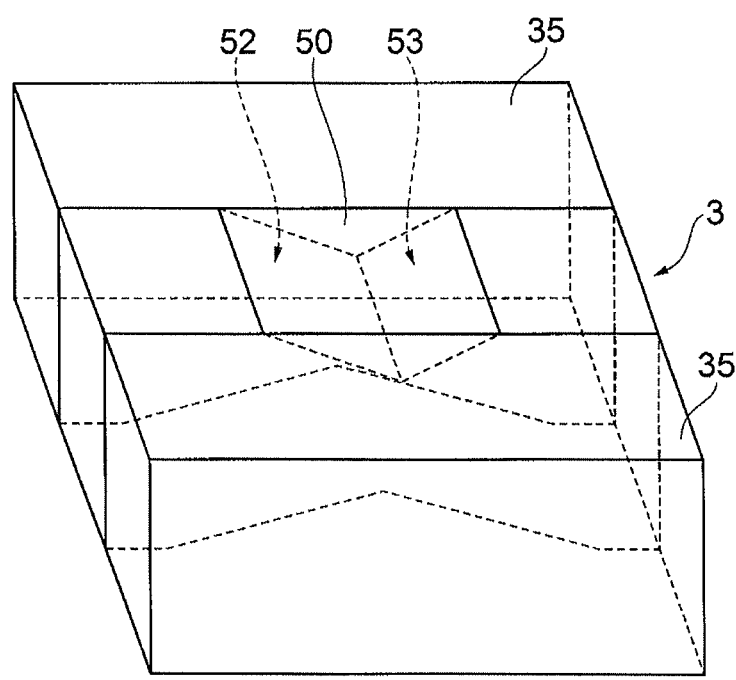
FIG. 3 is a perspective view of the integral prism illustrated in FIG. 2.

As illustrated in FIG. 3, blocks 35, 35 are bonded to both side faces of the integral prism 3, respectively. The blocks 35, 35 form walls on both sides of the depression 51a opening to both side faces of the integral prism, thereby allowing the depression 51a to be filled with the liquid 50. For securely preventing the liquid 50 from leaking out of the depression 51a filled therewith, it is preferred for the integral prism 3 and the block 35 to be bonded together with an adhesive made of silicone rubber or the like interposed therebetween.

Figure 4:
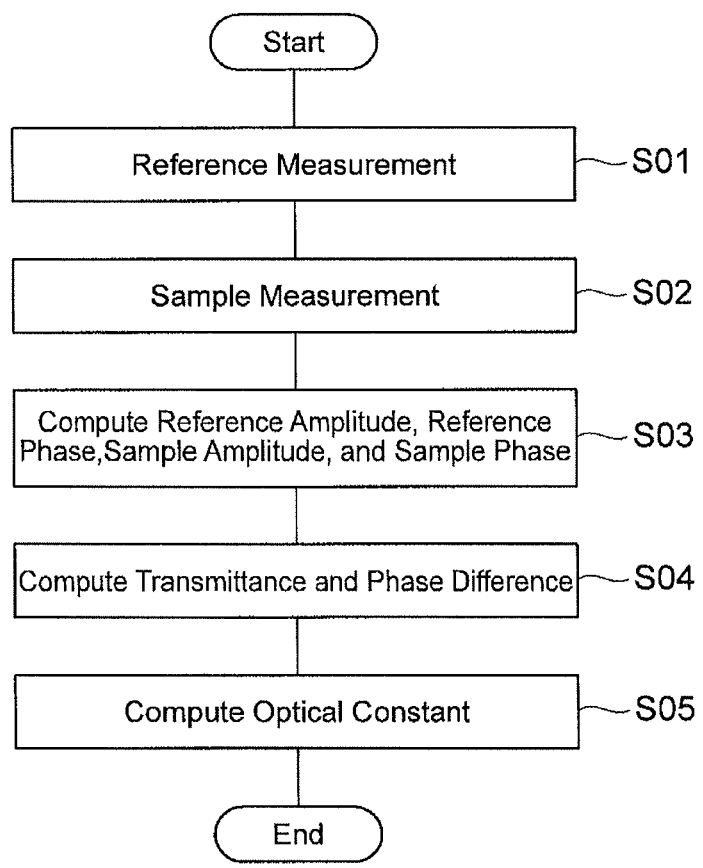
FIG. 4 is a flowchart illustrating a procedure of deriving an optical constant of an object to be measured.

FIG. 4 is a flowchart illustrating a procedure of deriving an optical constant of the object 34 by transmission spectrometry using the above-mentioned terahertz-wave spectrometer 1.

First, as illustrated in the flowchart, the terahertz-wave spectrometer 1 is used for performing reference measurement and sample measurement (steps S01 and S02). In the reference measurement, the depression 51a is filled with the liquid 50, and a substance (the liquid 50 here) having a known optical constant is measured. In the sample measurement, the object 34 is arranged in the depression 51a filled with the liquid 50, so as to measure a substance to obtain an optical constant. Subsequently, a reference measurement result $T_{ref}$ and a sample measurement result $T_{sig}$ are Fourier-transformed, so as to determine a reference amplitude $R_{ref}$, a reference phase $\phi_{ref}$, a sample amplitude $R_{sig}$, and a sample phase $\phi_{sig}$ (step S03).

Next, a transmittance T is determined by the following expression (1) according to the reference amplitude $R_{ref}$ and sample amplitude $R_{sig}$, and a phase difference Δ between the reference phase $\phi_{ref}$ and the sample phase $\phi_{sig}$ are determined by the following expression (2) (step S04).

[Math. 1]

$$T = \left|\frac{R_{sig}}{R_{ref}}\right|^2 \tag{1}$$

[Math. 2]

$$\Delta = \phi_{sig} - \phi_{ref} \tag{2}$$

These values are represented by using the complex refractive index of the object 34 (expression (3)) as the following expression (4). In expression (4), $t_{ref\,sig}$ and $t_{sig\,ref}$ are transmission Fresnel coefficients which are represented by the following expressions (5) and (6), respectively.

[Math. 3]

$$\tilde{n} = n + i\kappa \tag{3}$$

[Math. 4]

$$\tilde{t}(\omega) \equiv \sqrt{T(\omega)} \exp(i\Delta\phi(\omega)) = \tag{4}$$

$$t_{ref\,sig} \cdot t_{sig\,ref} \cdot \exp\left\{i\frac{(\tilde{n}_{sig}(\omega) - \tilde{n}_{ref}(\omega))d\omega}{c}\right\}$$

-continued

[Math. 5]
$$t_{ref\ sig} = \frac{2\tilde{n}_{ref}}{\tilde{n}_{ref} - \tilde{n}_{sig}} \quad (5)$$

[Math. 6]
$$t_{sig\ ref} = \frac{2\tilde{n}_{sig}}{\tilde{n}_{sig} + \tilde{n}_{ref}} \quad (6)$$

Therefore, the complex refractive index of the object 34 can be determined from the simultaneous equations of the following expressions (7) and (8), whereby a desirable optical constant of the object 34 is derived (step S05).

[Math. 7]
$$n_{sig}(\omega) = \frac{c}{d\omega}\left[\Delta\phi(\omega) + \frac{d\omega}{c} - \arg(t_{ref\ sig} \cdot t_{sig\ ref})\right] \quad (7)$$

[Math. 8]
$$\kappa_{sig}(\omega) = -\frac{c}{2d\omega}\ln\left[\frac{T(\omega)}{|t_{ref\ sig} \cdot t_{sig\ ref}|^2}\right] = -\frac{c}{2d\omega}\ln\left[\frac{T(\omega)}{|1 - r_{ref\ sig}^2|^2}\right] \quad (8)$$

In the terahertz-wave spectrometer 1, as explained in the foregoing, the arrangement part 31c to be arranged with the object 34 in the spectroscopic prism 31 is the depression 51a, which is filled with the liquid 50 incapable of dissolving the object 34 therein. Therefore, in a path of the terahertz wave T impinging on the first optical surface 31d and then passing through the arrangement part 31c toward the second optical surface 31e, the terahertz wave T can be kept from traveling through air.

This can eliminate the influence of absorption by the moisture in the air, thereby improving the measurement accuracy in spectrometry. The depression 51a may have various forms but can easily be filled with the liquid 50 regardless of the forms, whereby the convenience of measurement is maintained.

The depression includes the first refractive surface 52 for refracting the terahertz wave T from the first optical surface 31d toward the object 34 and the second refractive surface 53 for refracting the terahertz wave T transmitted through the object 34 toward the second optical surface 31e. When refracting P-polarized light at an interface between media having different refractive indexes, appropriately setting the angle of incidence with respect to the interface can reduce reflection loss as compared with the case where the light is perpendicularly incident on the interface and transmitted therethrough without refraction. This is clear from the fact that the reflectance of light transmitted through the interface between media having different refractive indexes is calculated by the following expressions (9) and (10):

[Math. 9]
$$r_p = \frac{n_b\cos\theta_a - n_a\cos\theta_b}{n_b\cos\theta_a + n_a\cos\theta_b} \quad (9)$$

[Math. 10]
$$R_p = |r_p|^2 \quad (10)$$

where
$r_p$ is the amplitude reflection coefficient for the P-polarized light;
$R_p$ is the reflectance for the P-polarized light;
$\theta_a$ is the incidence angle of light onto the interface;
$\theta_b$ is the exit angle of light from the interface;
$n_a$ is the refractive index of the medium on the light entrance side; and
$n_b$ is the refractive index of the medium on the light exit side.

Therefore, the reflection loss of the terahertz wave T directed from the first optical surface 31d to the object 34 can be reduced when the depression 51a includes the first refractive surface 52, while the reflection loss of the terahertz wave T passing through the object 34 toward the second optical surface 31e can be reduced when the depression includes the second refractive surface 53. For example, in the case where the refractive index of the spectroscopic prism 31 and the liquid 50 filling the depression 51a have refractive indexes of 3.4 and 1.4, respectively, the reflection loss occurring when the terahertz wave is made perpendicularly incident on the interface between the spectroscopic prism 31 and the liquid 50 reaches 31.8% on the entrance and exit sides of the liquid 50 in total. When the depression 51a includes the first and second refractive surfaces 52, 53, by contrast, appropriately setting the angles of the first and second refractive surfaces 52, 53 can cut down the reflection loss to about 0.1%. This can more securely eliminate the influence of the reflection loss of the terahertz wave, thereby further improving the measurement accuracy in spectrometry.

Figure 5:
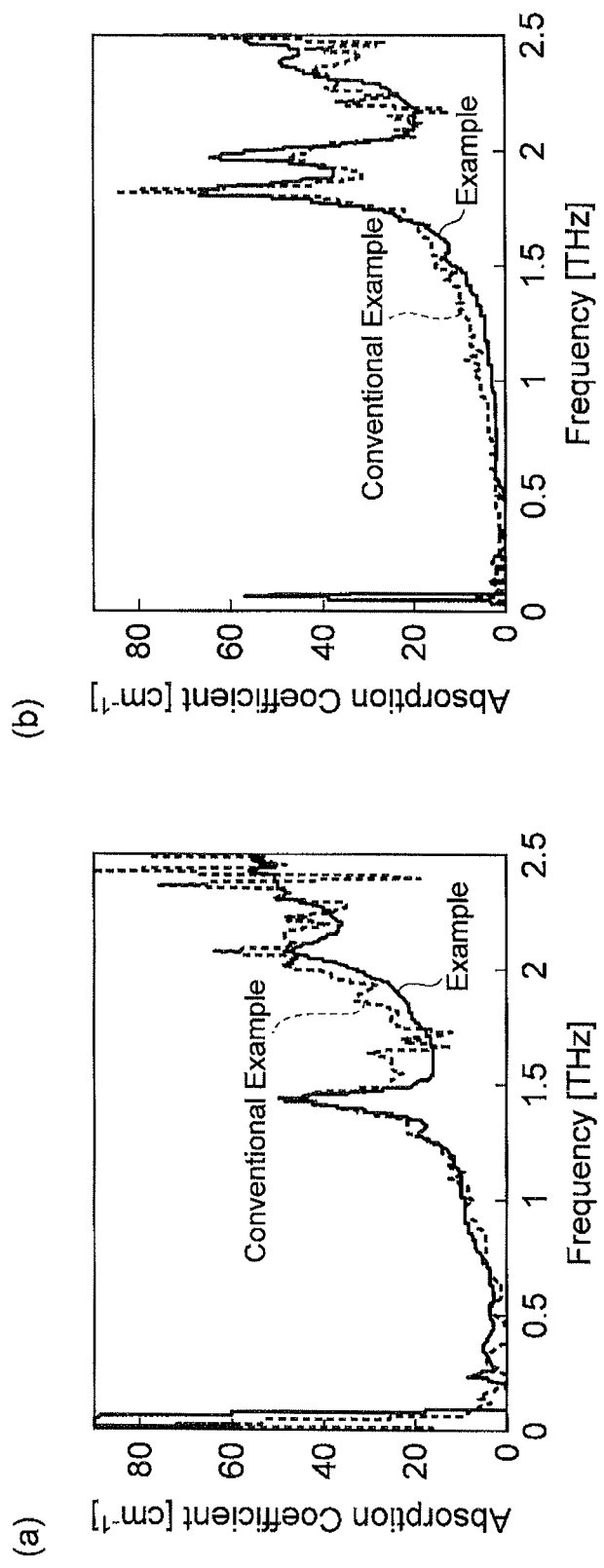
FIG. 5 is a set of charts illustrating results of measuring absorption coefficients of objects to be measured by the terahertz-wave spectrometer illustrated in FIG. 1.

FIG. 5 is a set of charts illustrating results of measuring absorption coefficients of the object 34 by using the terahertz-wave spectrometer. FIG. 5(a) is a chart when using glucose anhydrate as the object 34, and FIG. 5(b) is a chart when using glucose hydrate as the object 34. The plotted conventional example was acquired when the object arranged in air without using the integral prism 3 was irradiated with the terahertz wave.

The results illustrated in the charts show that, in each sample, the example eliminates the influences of absorption by moisture in the air and the influence of the reflection loss, so as to improve the S/N ratio as compared with the conventional example, thereby yielding vivid absorption peaks in the absorption curve. In the example, the object 34 is insoluble to the liquid 50, from which it can be determined that the obtained absorption coefficient is an absorption coefficient inherent in the substance of the object 34. This also makes it possible to reuse the object 34 after the measurement.

Figure 6:
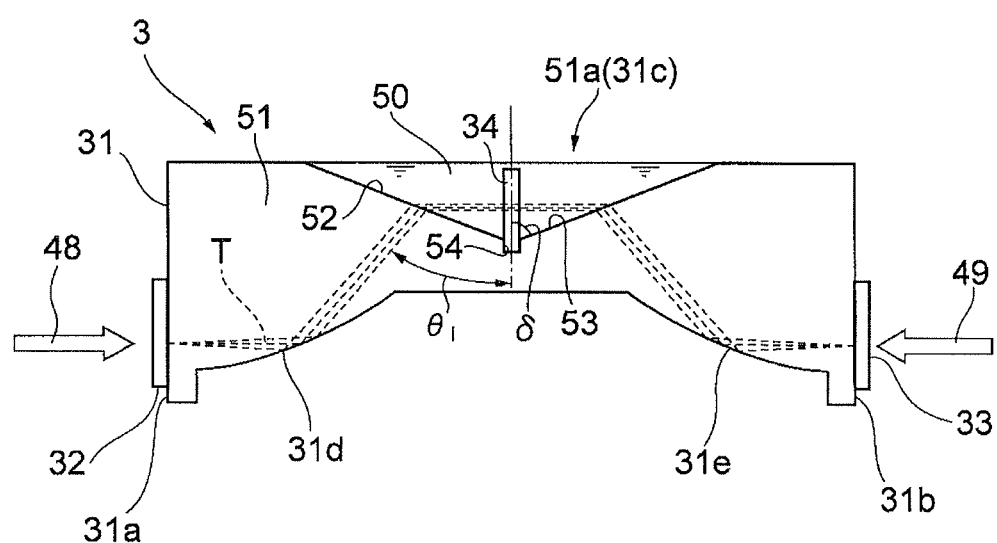
FIG. 6 is a side view illustrating a modified example of a spectroscopic prism.
Figure 7:
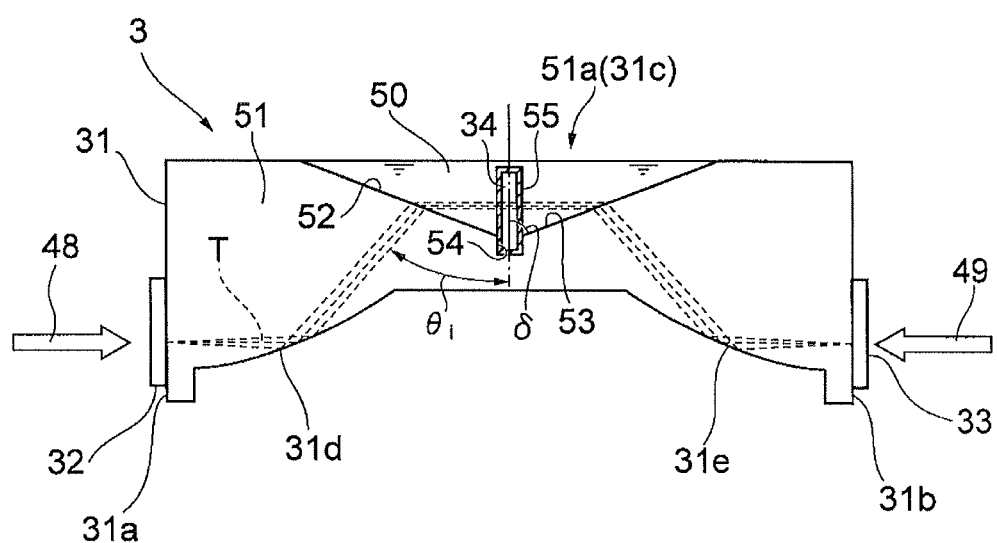
FIG. 7 is a side view illustrating another modified example of the spectroscopic prism.

The present invention is not limited to the above-mentioned embodiment. FIGS. 6 and 7 are diagrams illustrating modified examples of the spectroscopic prism. In the example illustrated in FIG. 6, the solid object 34 is formed into a disk, for instance. The apex of the bottom portion of the depression 51a forming the arrangement part 31c is provided with a recess for fitting the lower part of the object 34, whereby the spectroscopic prism 31 is formed with a support part 54 for supporting the object 34. This can stabilize the posture of the object 34 within the arrangement part 31c, thereby further improving the measurement accuracy. The solid object 34 may be secured to a holder, whose bottom part is supported by the support part 54.

In an example illustrated in FIG. 7, a disk-shaped cell 55 is filled with the liquid object 34, for instance. The spectroscopic prism 31 is formed with the support part 54 similar to that in FIG. 6, and the lower part of the cell 55 is fitted into the recess, whereby the cell 55 is supported. This makes the object 34 easy to arrange into and take out from the arrangement part 31c when the object 34 is a liquid.

Figure 8:
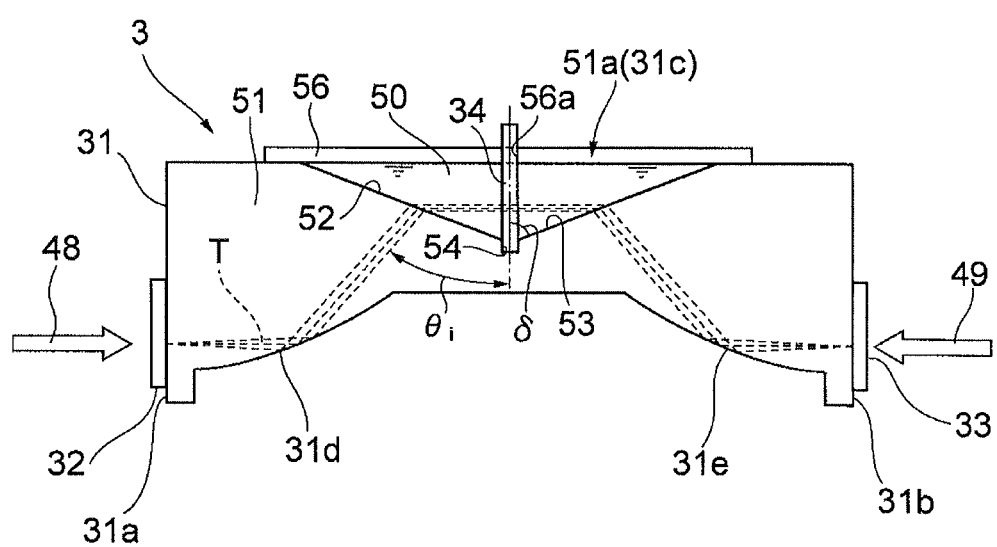
FIG. 8 is a side view illustrating still another modified example of the spectroscopic prism.

The apex of the bottom portion of the arrangement part 31c may also be formed with a flat part as the support part 54 for the object 34 or cell 55. As illustrated in FIG. 8, an opening 56a may be formed in a plate-like member 56 larger than the width of the depression 51a, and the plate-like member 56 having the object 34 or cell 55 inserted in the opening 56a may cover the depression 51a, so as to support the object 34 or cell 55. The plate-like member 56 may be provided with a slide mechanism which can adjust the width of the opening 56a.

Figure 9:
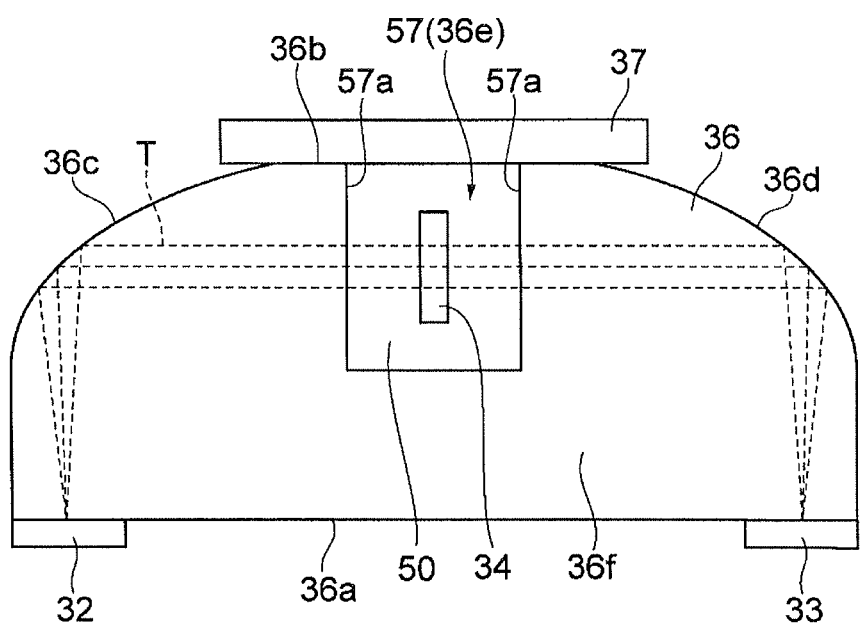
FIG. 9 is a plan view illustrating yet another modified example of the spectroscopic prism.

FIG. 9 is a diagram illustrating yet another modified example of the spectroscopic prism. In a spectroscopic prism 36 illustrated in FIG. 9, a side face 36a serving as both entrance and exit surfaces is provided on one side, the first and second optical surfaces 36c, 36d are provided on both flanks of a side face 36b opposite from the side face 36a, and an arrangement part 36e is provided at the center of the side face 36b. The terahertz-wave generator 32 and terahertz-wave detector 33 are integrally secured to the side face 36a so as to be juxtaposed horizontally. The first optical surface 36c is disposed such as to reflect and collimate the terahertz wave T generated in the terahertz-wave generator 32 within the spectroscopic prism 36. The second optical surface 36d is disposed such as to reflect the terahertz wave T collimated by the first optical surface 36c, so as to condense it toward the terahertz-wave detector 33.

The arrangement part 36e is constituted by a depression 57 formed at the center of the side face 36b. The depression 57 opens not only to the side face 36b of the spectroscopic prism 36, but also to its upper face 36f, thereby exhibiting a rectangular form in planar view. A plate material 37 is bonded to the side face 36b of the spectroscopic prism 36. This forms a wall on the side face 36b side of the depression 57, thereby allowing the depression 57 to be filled with the liquid 50 from thereabove. Two side faces 57a, 57a of the depression 57 opposing each other are disposed perpendicular to the path of the terahertz wave T directed from the first optical surface 36c to the second optical surface 36d.

Figure 10:
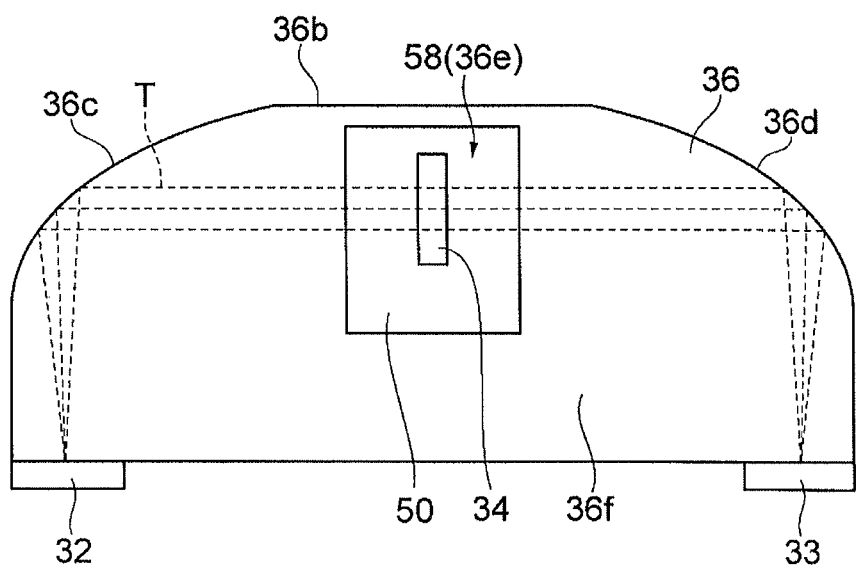
FIG. 10 is a plan view illustrating a further modified example of the spectroscopic prism.

In this spectroscopic prism 36, the terahertz wave T is perpendicularly incident on the two side faces 57a, 57a serving as the interfaces between the spectroscopic prism 36 and the liquid 50 and passes through the liquid 50 without refraction. In place of the depression 57 in the example of FIG. 9, a depression 58 opening to only the upper face 36f of the spectroscopic prism 36 may be provided as illustrated in FIG. 10. This enables the depression 58 to be filled with the liquid 50 without bonding the plate material 37 to the spectroscopic prism 36.

INDUSTRIAL APPLICABILITY

The present invention can be utilized in transmission spectrometry.

REFERENCE SIGNS LIST

1: terahertz-wave spectrometer; 2: laser light source; 3: integral prism; 13: beam splitter (branching unit); 31: spectroscopic prism (prism member); 31a: entrance surface; 31b: exit surface; 31c: arrangement part; 31d: first optical surface; 31e: second optical surface; 32: terahertz-wave generator; 33: terahertz-wave detector; 34: object to be measured; 48: pump light; 49: probe light; 51a: depression; 52: first refractive surface; 53: second refractive surface; 54: support part; 55: cell; T: terahertz wave

The invention claimed is:

1. A prism member for use in transmission spectrometry of an object to be measured employing a terahertz wave, the prism member comprising:
   an entrance surface for arranging a terahertz-wave generator for generating a terahertz wave in response to pump light incident thereon;
   an arrangement part for arranging the object;
   an exit surface for arranging a terahertz-wave detector for detecting a correlation between the terahertz wave transmitted through the object in the arrangement part and probe light;
   a first optical surface for collimating or condensing the terahertz wave incident thereon from the entrance surface toward the arrangement part; and
   a second optical surface for condensing the terahertz wave transmitted through the arrangement part toward the exit surface;
   wherein the arrangement part forms a depression adapted to be filled with a liquid incapable of dissolving the object therein, and
   wherein the depression includes a first refractive surface for refracting the terahertz wave from the first optical surface toward the object and a second refractive surface for refracting the terahertz wave transmitted through the object toward the second optical surface.

2. A prism member according to claim 1, wherein the object is a solid, and wherein the arrangement part has a support part for supporting the object.

3. A prism member according to claim 1, wherein the object is a liquid, and wherein the arrangement part has a support part for supporting a cell containing the object.

4. A terahertz-wave spectrometer for performing transmission spectrometry of an object to be measured by using a terahertz wave, the spectrometer comprising:
   a light source for emitting laser light;
   a branching unit for splitting the laser light emitted from the light source into pump light and probe light; and
   a prism member;
   wherein the prism member has:
      an entrance surface for arranging a terahertz-wave generator for generating a terahertz wave in response to the pump light incident thereon;
      an arrangement part for arranging the object;
      an exit surface for arranging a terahertz-wave detector for detecting a correlation between the terahertz wave transmitted through the object in the arrangement part and the probe light;
      a first optical surface for collimating or condensing the terahertz wave incident thereon from the entrance surface toward the arrangement part; and
      a second optical surface for condensing the terahertz wave transmitted through the arrangement part toward the exit surface;
      wherein the arrangement part forms a depression adapted to be filled with a liquid incapable of dissolving the object therein, and
   wherein the depression includes a first refractive surface for refracting the terahertz wave from the first optical surface toward the object and a second refractive surface for refracting the terahertz wave transmitted through the object toward the second optical surface.

5. A terahertz-wave spectrometer according to claim 4, wherein the object is a solid, and wherein the arrangement part has a support part for supporting the object.

6. A terahertz-wave spectrometer according to claim 4, wherein the object is a liquid, and wherein the arrangement part has a support part for supporting a cell containing the object.

7. A terahertz-wave spectrometric method for performing transmission spectrometry of an object to be measured by using a terahertz wave, the method using a prism member having:
- an entrance surface for arranging a terahertz-wave generator for generating a terahertz wave in response to pump light incident thereon,
- an arrangement part for arranging the object,
- an exit surface for arranging a terahertz-wave detector for detecting a correlation between the terahertz wave transmitted through the object in the arrangement part and probe light,
- a first optical surface for collimating or condensing the terahertz wave incident thereon from the entrance surface toward the arrangement part, and
- a second optical surface for condensing the terahertz wave transmitted through the arrangement part toward the exit surface,
- wherein the arrangement part forming a depression adapted to be filled with a liquid incapable of dissolving the object therein; and the method comprising:
- arranging the object in a state where the depression is filled with the liquid incapable of dissolving the object therein; and
- measuring an optical constant concerning the object according to the terahertz wave transmitted through the object,
- wherein the prism member has the arrangement part constituted by the depression including a first refractive surface for refracting the terahertz wave from the first optical surface toward the object and a second refractive surface for refracting the terahertz wave transmitted through the object toward the second optical surface.

8. A terahertz-wave spectrometric method according to claim 7, wherein the object is a solid, and wherein the prism member has a support part for supporting the object in the arrangement part.

9. A terahertz-wave spectrometric method according to claim 7, wherein the object is a liquid, and wherein the prism member has a support part for supporting a cell containing the object.

10. A terahertz-wave spectrometric method according to claim 7, wherein a liquid incapable of absorbing the terahertz wave is used as the liquid incapable of dissolving the object therein.

11. A terahertz-wave spectrometric method according to claim 7, wherein a fluorine-based inert liquid is used as the liquid incapable of dissolving the object therein.

12. A terahertz-wave spectrometric method according to claim 7, wherein a silicone oil is used as the liquid incapable of dissolving the object therein.

* * * * *